United States Patent [19]

Schneider et al.

[11] 4,202,821

[45] May 13, 1980

[54] N-(N'-METHYLENEPYRROLIDONYL)-2-SUBSTITUTED ANILINES

[75] Inventors: Louis Schneider, Elizabeth; David E. Graham, Westfield, both of N.J.

[73] Assignee: GAF Corporation, New York, N.Y.

[21] Appl. No.: 969,358

[22] Filed: Dec. 14, 1978

Related U.S. Application Data

[63] Continuation-in-part of Ser. No. 955,483, Oct. 27, 1978, Ser. No. 942,644, Sep. 15, 1978, Pat. No. 4,153,446, Ser. No. 935,354, Aug. 21, 1978, Ser. No. 928,569, Jul. 27, 1978, and Ser. No. 892,146, Mar. 31, 1978.

[51] Int. Cl.$^2$ .................... A01N 9/22; C07D 207/26
[52] U.S. Cl. ............................... 260/326.5 S; 71/95; 260/326.5 FL
[58] Field of Search ................ 260/326.5 S, 326.5 FL

[56] References Cited

U.S. PATENT DOCUMENTS 3,769,301  10/1973  Olin .................................. 260/326.45
3,907,544  9/1975   Olin .......................................... 71/95

Primary Examiner—Alton D. Rollins
Assistant Examiner—Lisa Jones
Attorney, Agent, or Firm—Walter C. Kehm; Walter Katz

[57] ABSTRACT

This invention relates to novel N-(N'-methylenepyrrolidonyl)-2-substituted anilines which are useful intermediates in the synthesis of herbicides.

The intermediate compounds of the invention have the formula:

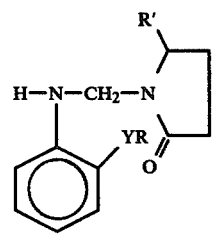

Where
R is alkyl, $C_1$–$C_6$, alkenyl, $C_3$–$C_5$, alkyleneoxyalkyl, —$(CH_2)_nOR''$, where n=1–3, and R'' is alkyl, $C_1$–$C_3$, and cycloalkyl,

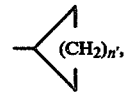

where n'=0–3,
R' is hydrogen or alkyl, $C_1$–$C_3$, and,
Y is oxygen or sulfur.

21 Claims, No Drawings

N-(N'-METHYLENEPYRROLIDONYL)-2-SUBSTITUTED ANILINES

This application is a continuation-in-part of Ser. Nos. 892,146, filed Mar. 31, 1978; 928,569 filed July 27, 1978; 935,354, filed Aug. 21, 1978; 955,483, filed Oct. 27, 1978; and 942,644, filed Sept. 15, 1978, now U.S. Pat. No. 4,153,446.

BACKGROUND OF THE INVENTION

1. Field of the Invention

This invention relates to novel N-(N'-methylenepyrrolidonyl)-2-substituted anilines which are useful intermediates in making agricultural herbicides.

2. Description of the Prior Art

U.S. Pat. Nos. 3,769,301 and 3,907,544 disclose related herbicidal compounds; however, these compounds are made by a different process, and accordingly, they do not disclose the intermediates of the invention for the synthesis of such herbicidally active compounds.

SUMMARY OF THE INVENTION

This invention relates to novel N-(N'-methylenepyrrolidonyl)-2-substituted aniline intermediate compounds having the formula:

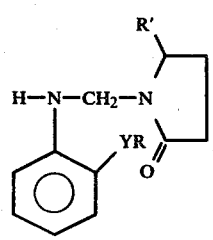

where
R is alkyl, $C_1$–$C_6$, alkenyl, $C_3$–$C_5$, alkyleneoxyalkyl, —$(CH_2)_nOR''$ where n=1–3, and R'' is alkyl, $C_1$–$C_3$, cycloalkyl,

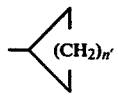

where n'=0–3
R' is hydrogen or alkyl, $C_1$–$C_3$, and
Y is oxygen or sulfur.

DETAILED DESCRIPTION OF THE INVENTION

The starting materials for making the intermediates of this invention are 2-substituted anilines which are usually commercially available; otherwise they are made from 2-nitrophenol or 2-nitrothiophenol by reaction with a halogenated alkyl ether, a cycloalkyl halide, an alkyl halide or an alkenyl halide to form the 2-substituted oxynitrobenzene or 2-substituted thionitrobenzene. The nitro group then is reduced to the corresponding aniline.

The next step in the process of preparation of the intermediates of the invention is the reaction of the aniline with N-methylolpyrrolidone or N-chloromethylpyrrolidone to form the desired N-(N'-methylenepyrrolidonyl)-2-substituted aniline. For N-methylolpyrrolidone, this step is carried out to provide the intermediate compound in high yield by heating a reaction mixture containing substantially equivalent molar amounts of the reactants in a solvent, such as an aromatic hydrocarbon, under non-catalyzed conditions, at a reflux temperature of about 80°–140° C., while simultaneously and continuously distilling out an azeotrope consisting essentially of water and solvent until substantially a stoichiometric amount of water produced during the reaction has been removed thereby. The desired intermediate compound then is crystallized from the remaining solution.

For N-chloromethylpyrrolidone, the reaction is carried out in a solvent in the presence of an acid acceptor, at about room temperature. The use of N-chloromethylenepyrrolidone as the alkylating agent is particularly useful for forming 2-substituted derivatives which are sensitive to heat, such as the alkenyl group.

The intermediate compounds of the invention are acylated with a haloacetyl halide to form N-(haloacetyl) compounds which are useful herbicides.

As used herein, the term "alkyl" includes both straight and branched chain hydrocarbon radicals; and the term "alkenyl" includes straight, branched chain and cyclic hydrocarbons.

Preparation of N-Methylolpyrrolidone

2-Pyrrolidone (212.4 g., 2.0 mole) and potassium hydroxide (0.6 g) is heated to 80° C. and paraformaldehyde (75.6 g, 2.6 mole) were added during 10 minutes, and the mixture was maintained at 75°–80° C. for ½ hour. The desired product then was crystallized from 1 part of benzene to yield 227 g. (88.2%), m.p. 78°–80° C. of product.

Preparation of N-Chloromethylpyrrolidone

N-Methylolpyrrolidone (225 g., 1.95 mole) and toluene (400 cc) were chilled to 5° C. with stirring and thionyl chloride (257 ml., 3.3 mole) in toluene (300 cc) was added dropwise in 2 hrs. and the mixture allowed to remain overnight. The toluene solvent then was rotoevaporated and the residue distilled at 107°–110° C. at 2.5–3 mm. Hg . yielding 151.5 g (58.2%) of product which crystallized on standing, m.p. 35°–37° C.

EXAMPLE 1

N-(N'Methylene-2-Pyrrolidonyl)-2-Methoxyaniline

2-Methoxyaniline (24.6 g., 0.2 mole), xylene (100 cc) and N-methylolpyrrolidone (23.0 g., 0.2 mole) were refluxed while an azeotrope containing a stoichiometric amount of water is removed. The product then was crystallized from xylene-ether, and vacuum dried, to yield 172 g. (89%), m.p. 106°–108° C. of product.

EXAMPLE 2

N-(N'-Methylene-2-Pyrrolidonyl)-2-sec-Butoxyaniline

A mixture of o-sec-butoxyaniline (32 g., 0.19 mole), N-methylol-2-pyrrolidone (21.9 g., 0.19 mole), and xylene (100 ml) were refluxed under azeotropic conditions for about 1¾ hours and about 2 ml. of water was collected. The xylene solution was washed with 5% hydrochloric acid followed by three water washes. The xylene layer was dried over magnesium sulfate and the solvent removed by rotoevaporation yielding 46.5 g. (97.8%) product.

EXAMPLE 3

N-(5-Methyl-N'-Methylene-2-Pyrrolidonyl)-2-Ethoxyaniline

A mixture of 5-methyl-N-hydroxymethyl-2-pyrrolidone (25.8 g., 0.20 moles), o-ethoxyaniline (27.5 g, 0.20 moles), and xylene (81 ml.) were refluxed for 1 hour while removing water; then an additional 3 hours. The xylene was removed by rotoevaporation and the residue crystallized on standing. Recrystallized from methanol provided 25.9 g of product (52.1% yield) m.p. 89°–91° C.

EXAMPLE 4

N-(N'-Methylene-2-Pyrrolidonyl)-2-Cyclopentoxyaniline

A. 2-Cyclopentoxynitrobenzene

2-Nitrophenol (83.5 g, 0.60 mole), cyclopentyl bromide (98.0 g, 0.66 mole), anhydrous potassium carbonate (82.9 g, 0.60 mole) and dry acetone (600 cc) were refluxed for 72 hours, and filtered to remove the potassium bromide. The residue was washed with acetone and the solvent was removed by rotary evaporation. The residue was partitioned between 200 cc of dichloromethane and water. The dichloromethane layer was washed with 200 cc of 10% potassium hydroxide, separated and the solvent was removed by rotary evaporation. The crude product was fractionally distilled at 144°–146° C. at 1.0 mm. Hg to yield 58.2 g of product (46.8%).

B. 2-Cyclopentoxyaniline

Iron 60 mesh (51.9 g, 0.93 mole), water (220 cc), ethanol (244 cc) and concentrated hydrochloric acid (14.2 cc) were heated to reflux under a nitrogen blanket. Then 2-cyclopentoxynitrobenzene (55.2 g, 0.27 mole) was added at reflux over a period of 2 hours. The reaction was maintained at reflux for an additional 3 hours. The pH was adjusted to 7–8 by the addition of concentrated ammonium hydroxide. The reaction mixture then was filtered at 30° C., and the filtrate was washed with 200 cc of ether. The filtrate was extracted with 4×50 cc of ether and the combined ether extracts were subjected to rotary evaporation. The crude product was fractionally distilled at 126°–130° C. at 2.0–2.5 mm. Hg to yield 30.3 g (64.3%) of product.

C. 2-Cyclopentoxyaniline (10.0 g, 0.057 mole), N-methylol-2-pyrrolidone (9.75 g, 0.85 mole) and xylene (25 cc) were refluxed under azeotropic conditions with the removal of 1.5 cc of water. The xylene was removed by rotary evaporation and the product was crystallized from 100 cc of hexane to yield 8.0 g (51.6%) of product, m.p. 87°–87.5° C.

EXAMPLE 5

N-(5-Methyl-N'-Methylene-2-Pyrrolidonyl)-2-Methylmercaptoaniline

2-Methylmercaptoaniline, 5-methyl-N-hydroxymethyl-2-pyrrolidone and toluene were reacted in a similar manner as described in Example 1.

EXAMPLE 6

N-(N'-Methylenepyrrolidonyl)-2-Isopropylmercaptoaniline

A. 2-Isopropylmercaptoaniline

2-Nitrothiophenol, 2-bromopropane, potassium carbonate and acetone were refluxed for several hours. The solvent then was removed by rotary evaporation. The crude product was partitioned between methylene chloride and a 10% sodium carbonate solution. The organic phase was distilled to yield 2-isopropylmercaptonitrobenzene.

B. This intermediate was reduced to the corresponding aniline by reduction with iron, concentrated hydrochloric acid and ethanol. The mercaptoaniline was isolated by vacuum distillation.

C. 2-Isopropylmercaptoaniline and, N-methylolpyrrolidone were condensed in toluene with the removal or water as described in Example 1.

EXAMPLE 7

N-(N'-Methylene-2-Pyrrolidonyl)-2-Butylmercaptoaniline

2-Butylmercaptoaniline was prepared from -2-nitrothiophenol by a two-step reaction sequence consisting of alkylation followed by reduction corresponding to the procedure described in Example 4. The aniline then was condensed with N-methylol-2-pyrrolidone to yield the desired product.

EXAMPLE 8

N-(N'-Methylene-2-Pyrroldonyl)-2-Propen-2-yl-mercaptoaniline

2-Propen-2-yl-mercaptoaniline was prepared by reduction of 2-propen-2-yl-mercaptonitrobenzene, which was obtained by condensing 2-nitrothiophenol and allyl bromide, to give the corresponding aniline.

Then 2-propen-2-yl-mercaptoaniline and N-methylol-2-pyrrolidone were condensed in toluene with the removal of water to form the desired product.

EXAMPLE 9

(N-(N'-Methylene-2-Pyrrolidonyl)-2-Ethoxyethylmercaptoaniline

2-Ethoxyethylmercaptoaniline was prepared by reduction of 2-ethoxyethylmercaptonitrobenzene, which was obtained by condensation of 2-nitrothiophenol and 2-bromoethyl ethyl ether to give the corresponding aniline. The 2-ethoxyethylmercaptoaniline and N-methylol-2-pyrrolidone were then condensed in toluene with the removal of water to form the methylenepyrrolidonylaniline in high yield.

EXAMPLE 10

N-(N'-Methylene-2-Pyrrolidonyl)-2-Cyclopentylmercaptoaniline

2-Cyclopentylmercaptoaniline was prepared by reduction of 2-cyclopentylmercaptonitrobenzene, which was obtained from 2-nitrothiophenol and bromocyclopentane followed by reduction to the corresponding aniline. The 2-cyclopentylmercaptoaniline was subsequently condensed in toluene with the removal of water to form the desired product in high yield.

EXAMPLE 11

N-(N'-Methylene-2-Pyrrolidonyl)-2-Methylmercaptoaniline

2-Methylmercaptoaniline (50.0 g, 0.36 mole), N-methylol-2-pyrrolidone (41.3 g, 0.36 mole) and toluene (145 cc) were refluxed under azeotropic conditions until the stoichiometric amount of water was removed. The reaction was washed successively with 100 cc of 10% hydrochloric acid, 100 cc of 10% sodium carbonate and finally with water. The toluene phase was dried over magnesium sulfate and removed by rotary evaporation. The product (69 g, 81.5% yield) was isolated as an oil.

EXAMPLE 12

N-(N'-Methylene-2-Pyrrolidonyl)-2-Ethylmercaptoaniline

2-Ethylmercaptoaniline, N-methylol-2-pyrrolidone and toluene were condensed with the removal of water to form the desired product.

EXAMPLE 13

N-(N'-Methylene-2-Pyrrolidonyl)-2-Ethoxyethoxyaniline

A. 2-Ethoxyethoxynitrobenzene

2-Nitrophenol (91.0 g., 0.65 mole), 2-bromoethyl ethyl ether (100.0 g., 0.65 mole), anhydrous potassium carbonate (9.0 g, 0.72 mole), and acetone (1 liter) were refluxed for 65 hours. The reaction mixture was filtered, and the acetone removed by rotary evaporation. The residue was partitioned between 200 ml. of dichloromethane and 100 ml water. The organic phase was further washed with 200 ml. of 10% sodium hydroxide followed by 100 cc of water. The product (58.0 g) was obtained in 42% yield by a vacuum distillation (100°–120° C./0.5 mm).

B. 2-Ethoxyethoxyaniline

Iron 60 mesh (54.0 g, 0.96 mole), concentrated hydrochloric acid (15 cc), ethanol (260 cc) and water (230 cc) were heated to reflux under a nitrogen blanket; 2-ethoxyethoxynitrobenzene (58.0 g, 0.28 mole) was added at reflux over 4 hours, and reflux continued for an additional 3 hours. The reaction mixture then was neutralized with concentrated ammonium hydroxide to a pH of 8–9, and filtered through a Celite bed. The iron cake was washed with 200 cc of ether, and the organic phase was separated. The product (20.0 g) was obtained in 40.2% yield by a vacuum distillation (111°–135° C./2–4 mm.)

C. 2-Ethoxyethoxyaniline (20.0 g, 0.11 mole), N-methylol-2-pyrrolidone (13.5 g., 0.11 mole) and 100 cc xylene were refluxed under azeotropic conditions until the stoichiometric amount of water was removed (1.0 cc). The xylene layer then was washed with 2×50 cc of water, dried over magnesium sulfate and filtered. The xylene was removed by rotary evaporation. The crude product was solubilized in dichloromethane, and purified by column chromatography, using a 2.4:5.6:2.0 chloroform:hexane:acetone solvent system to yield 16.2 g of product; 53% yield.

EXAMPLE 14

N-(N'-Methylene-2-Pyrrolidonyl)-2-Propoxymethoxyaniline

2-Nitrophenol, bromomethyl propyl ether, anhydrous potassium carbonate and acetone were reacted according to the procedure outlined in Example 1 to yield 2-propoxymethoxynitrobenzene, which was reduced to the corresponding aniline, and isolated by a vacuum distillation.

2-Propoxymethoxyaniline, N-methylol-2-pyrrolidone and xylene then were condensed while removing water to form the product.

EXAMPLE 15

N-(N'-Methylene-2-Pyrrolidonyl)-2-Methoxypropoxyaniline

2-Nitrophenol, 3-bromopropyl methyl ether, anhydrous potassium carbonate and acetone were reacted according to the procedure outlined in Example 1 to yield 2-methoxypropoxynitrobenzene, which was reduced to the corresponding aniline. The aniline was isolated by vacuum distillation.

2-Methoxypropoxyaniline, N-methylol-2-pyrrolidone and xylene then were condensed while removing water to form the desired product.

EXAMPLE 16

N-(N'-Methylene-2-Pyrrolidonyl)-2-Prop-1-en-oxyaniline

A. 2-Prop-1-en-oxynitrobenzene

2-Nitrophenol (142.0 g, 1.02 mole), allyl bromide (120.9 g, 1.00 mole), anhydrous potassium carbonate (140.0 g, 1.02 mole) and dry acetone (500 cc) were refluxed for 21 hours, and filtered to remove the potassium bromide. The residue was washed with acetone and the solvent was removed by rotary evaporation. The residue was partitioned between 200 cc of dichloromethane and water. The dichloromethane layer was washed with 200 cc of 10% potassium hydroxide, separated and the solvent was removed by rotary evaporation. The crude product was fractionally distilled at 124° C. at 2.0 mm. Hg to yield 164.7 g of product (91.9%).

B. 2-Prop-1-en-oxyaniline

Iron 60 mesh (106.3 g, 1.9 mole), water (450 cc), ethanol (500 cc) and concentrated hydrochloric acid (29.5 cc) were heated to reflux under a nitrogen blanket. Then 2-prop-1-en-oxynitrobenzene (89.6 g, 0.57 mole) was added at reflux over a period of 2 hours. The reaction was maintained at reflux over a period of 2 hours. The reaction was maintained at reflux for an additional 3 hours. The pH was adjusted to 7–8 by the addition of concentrated ammonium hydroxide. The reaction mixture then was filtered at 30° C., and the filtrate was washed with 200 cc of ether. The filtrate was extracted with 4×50 cc of ether and the combined ether extracts were subjected to rotary evaporation. The crude product was fractionally distilled at 110°–112° C. at 4.5 mm. Hg to yield 50.1 g (67.2%) of product.

C. 2-Prop-1-en-oxyaniline (5.6 g., 0.037 mole), sodium carbonate (3.9 g, 0.037 mole) and toluene (50 ml) were chilled to 5° C. with stirring and N-chloromethylpyrrolidone (5.0 g., 0.037 mole) in toluene 20 cc) was added dropwise during ½ hour and allowed to stand overnight. Then 100 ml water was added to the mixture; the toluene layer was filtered, and rotoevaporated to give a crude product which was recrystallized form ether yielding 6.8 of product (75.0%), m.p. 79°–81° C.

EXAMPLE 17

N-(N'-Methylene-2-Pyrrolidonyl)-2-But-1-en-oxyaniline

4-Bromobutene-1was reacted with o-nitrophenol to yield 2-but-1-ene-oxynitrobenzene which was reduced to the corresponding aniline; and reacted with N-chloromethyl-2-pyrrolidone to form the corresponding N-methylenepyrrolidonyl derivative.

EXAMPLE 18

N-(N'-Methylene-2-Pyrrolidonyl)-2-Methylprop-1-en-oxyaniline

3-Chloro-2-methylpropene was reacted with o-nitrophenol to yield 2-(2-methylprop-1-en-oxy) nitrobenzene; which was reduced to the corresponding aniline; reacted with N-chloromethyl-2-pyrrolidone to form the corresponding N-methylenepyrrolidonyl derivative.

EXAMPLE 19

N-(N'-Methylene-2-Pyrrolidonyl)-2-But-2-en-oxyaniline

2-Bromo-but-2-ene was reacted with o-nitrophenol to yield 2-but-1-en-oxynitrobenzene; which was reduced to the corresponding aniline; then reacted with N-chloromethyl-2-pyrrolidone to form the corresponding N-methylene-2-pyrrolidonyl derivative.

EXAMPLE 20

N-5-Methyl-N'-Methylene-2-Pyrrolidonyl-2-Prop-1-ene-oxyaniline

Allyl bromide was reacted with o-nitrophenol to yield 2-prop-1-en-oxynitrobenzene; which was reduced to the corresponding aniline; then reacted with 5-methyl-N-chloromethyl-2-pyrrolidone to form the corresponding 5-methyl-N'-methylene-2-pyrrolidonyl derivative.

EXAMPLE 21

N-(5-Methyl-N'-Methylene-2-Pyrrolidonyl)-2-Cyclopent-3-en-oxyaniline

Cyclopent-3-en-1-ol was reacted with o-nitrophenol to yield 2-cyclopent-3-en-oxynitrobenzene; which was reduced to the corresponding aniline; then reacted with 5-methyl-N-chloromethyl-2-pyrrolidone to form the corresponding 5-methyl-N'-methylene-2-pyrrolidonyl derivative.

What we claim is:

1. N-(N'-methylenepyrrolidonyl)-2-substituted aniline intermediate compounds having the formula:

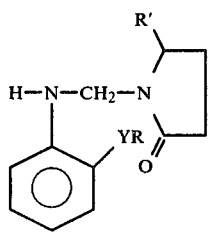

where

R is alkyl, $C_1$–$C_6$, alkenyl, $C_3$–$C_5$, alkyleneoxyalkyl, —$(CH_2)_nOR''$, where n=1–3, and R'' is alkyl, $C_1$–$C_3$, and cycloalkyl,

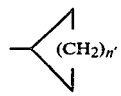

where n'=0–3,
R' is hydrogen or alkyl, $C_1$–$C_3$, and,
Y is oxygen or sulfur.

2. Compounds according to claim 1 where R is alkyl, $C_1$–$C_6$.

3. Compounds according to claim 1 wherein R is alkenyl, $C_3$–$C_5$.

4. Compounds according to claim 1 wherein R is alkyleneoxyalkyl, —$(CH_2)_nOR''$, where n=1–3, and R'' is alkyl, $C_1$–$C_3$.

5. Compounds according to claim 1 wherein R is cycloalkyl,

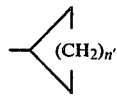

where n'=0–3.

6. Compounds according to claim 1 where R' is hydrogen.

7. Compounds according to claim 1 wherein R' is alkyl, $C_1$–$C_3$.

8. Compounds according to claim 1 wherein Y is oxygen.

9. Compounds according to claim 1 wherein Y is sulfur.

10. A compound according to claim 1 which is N-(N'-methylene-2-pyrrolidonyl)-2-methoxyaniline.

11. A compound according to claim 1 which is N-(N'-methylene-2-pyrrolidonyl)-2-sec-butoxyaniline.

12. A compound according to claim 1 which is N-(5-methyl-N'-methylene-2-pyrrolidonyl)-2-ethoxyaniline.

13. A compound according to claim 1 which is N-(N'-methylene-2-pyrrolidonyl)-2-cyclopentoxyaniline.

14. A compound according to claim 1 which is N-(5-methyl-N'-methylene-2-pyrrolidonyl)-2-methylmercaptoaniline.

15. A compound according to claim 1 which is N-(N'-methylenepyrrolidonyl)-2-isopropylmercaptoaniline.

16. A compound according to claim 1 which is N-(N'-methylene-2-pyrrolidonyl)-2-butylmercaptoaniline.

17. A compound according to claim 1 which is N-(N'-methylene-2-pyrrolidonyl)-2-propen-2-yl-mercaptoaniline.

18. A compound according to claim 1 which is N-(N'-methylene-2-pyrrolidonyl)-2-ethoxyethylmercaptoaniline.

19. A compound according to claim 1 which is N-(N'-methylene-2-pyrrolidonyl)-2-cyclopentylmercaptoaniline.

20. A compound according to claim 1 which is N-(N'-methylene-2-pyrrolidonyl)-2-methylmercaptoaniline.

21. A compound according to claim 1 which is N-(N'-methylene-2-pyrrolidonyl)-2-ethylmercaptoaniline.

* * * * *